United States Patent [19]
Modglin

[11] Patent Number: 5,620,412
[45] Date of Patent: *Apr. 15, 1997

[54] HIP ABDUCTION SYSTEM

[75] Inventor: Michael D. Modglin, Winter Haven, Fla.

[73] Assignee: National Orthotic Laboratories, Inc., Winter Haven, Fla.

[*] Notice: The term of this patent shall not extend beyond the expiration date of Pat. No. 5,344,391.

[21] Appl. No.: 489,830

[22] Filed: Jun. 13, 1995

Related U.S. Application Data

[63] Continuation of Ser. No. 310,989, Sep. 23, 1994, abandoned, which is a continuation of Ser. No. 185,412, Jan. 24, 1994, abandoned, which is a division of Ser. No. 911,477, Jul. 10, 1992, Pat. No. 5,344,391.

[51] Int. Cl.⁶ .................................................. A61F 5/00
[52] U.S. Cl. ............................... 602/24; 602/16; 602/19
[58] Field of Search .................... 602/5, 6, 16, 19, 602/23–25

[56] References Cited

U.S. PATENT DOCUMENTS

| | | | |
|---|---|---|---|
| 1,490,265 | 4/1924 | Glasgow | 602/23 |
| 2,181,689 | 11/1939 | Bell. | |
| 2,285,612 | 6/1942 | Rehthaler. | |
| 2,332,119 | 10/1943 | Springer | 602/19 |
| 2,397,709 | 4/1946 | Versoy et al.. | |
| 2,778,358 | 1/1957 | Keles | 602/19 X |
| 2,813,526 | 11/1957 | Beebe. | |
| 3,351,053 | 11/1967 | Stuttle. | |
| 3,441,027 | 4/1969 | Lehman. | |
| 3,605,731 | 9/1971 | Tigges. | |
| 4,202,327 | 5/1980 | Glancy | 602/19 |
| 4,475,543 | 10/1984 | Brooks et al.. | |
| 4,481,941 | 11/1984 | Rolfes. | |
| 4,497,315 | 2/1985 | Fettweis et al. | 602/19 |
| 4,531,515 | 7/1985 | Rolfes. | |
| 4,557,257 | 12/1985 | Fernandez et al. | 602/19 X |
| 4,574,790 | 3/1986 | Wellershaus | 602/23 X |
| 4,602,627 | 7/1986 | Vito et al. | 602/23 |
| 4,901,710 | 2/1990 | Meyer | 602/24 |
| 4,905,678 | 3/1990 | Cumins et al. | 602/19 X |
| 4,957,103 | 9/1990 | Young et al.. | |
| 5,012,798 | 5/1991 | Graf et al.. | |
| 5,038,760 | 8/1991 | Osborn. | |
| 5,054,476 | 10/1991 | Petrofsky et al. | 602/23 X |

*Primary Examiner*—Linda C. Dvorak
*Attorney, Agent, or Firm*—Rothwell, Figg, Ernst, & Kurz

[57] ABSTRACT

A substantially rigid hip abduction system is disclosed which provides support for the hip joint of a human patient while being comfortably worn, even during ambulation. The hip abduction system is a bi-valve structure including pelvic girdle having a first and a second hip engaging members and a front and rear slidable guides which facilitate precise positioning of the pelvic girdle and prevents vertical movement of the system. The hip abduction system of the present invention also includes elongated flanges on the pelvic girdle which substantially eliminates migration thereof on the patient.

5 Claims, 2 Drawing Sheets

HIP ABDUCTION SYSTEM

This is a continuation of application Ser. No. 08/310,989, filed Sep. 23, 1994, now abandoned, which is a continuation of Ser. No. 08/185,412, filed Jan. 24, 1994, now abandoned, which is a divisional of Ser. No. 07/911,477, filed Jul. 10, 1992, U.S. Pat. No. 5,344,391.

BACKGROUND OF THE INVENTION

Field of the Invention

This invention relates generally to orthopedic supports and braces and, more particularly, to a hip abduction system for stabilizing the a hip joint.

Background Art

Hip stabilizers or supports of various types have been employed for many years as devices for stabilizing a patient's hip joint who has suffered injury to the hip region or who has undergone a surgical procedure, such as hip replacement. Prior to the advent of hip stabilizers, a patient suffering from a hip injury was placed into a cast which stabilized the hip joint but virtually immobilized the patient. The casts were often bulky, heavy and cumbersome which made handling and transporting the patient very difficult. Additionally, completely immobilizing a patient during healing period often resulted in muscle atrophy and joint deterioration. To substantially eliminate these shortcomings, hip stabilization devices were created which both stabilized the hip joint while allowing limited movement to the thigh of the patient.

Hip stabilizers for many years have generally assumed the configuration of a corset or belt which were adapted to encircle a person's body in the waist area. These devices also comprised metal biasing structures for supporting the hip joint which were attached to a thigh support structure. For example, a hip stabilizer of this general type is described in U.S. Pat. No. 4,905,678 which shows an adjustable belt made of leather or mildly flexible plastic extending circumferentially around the patient. A metallic biasing structure is provided for biasing the thigh of a patient at a desired angle and for supporting the hip joint. The biasing structure is attached to a thigh engaging means which is an accurate shaped plastic support shaped to conform to the curvature of a patient's thigh.

Another known hip stabilizer is disclosed in U.S. Pat. No. 4,957,103 which utilizes an orthopedic body jacket including a semi-rigid thermoplastic shell adapted to be fitted around the abdomen of a patient. The body jacket has an opening along its ventral mid-line which enables the device to be placed around the patient which is fastened by an adjustable strap. The body jacket also includes an integrally molded matrix plate for adjustably securing an orthotic component such as a caliper.

Although providing greater mobility than casts, many deficiencies have been recognized with the above-described hip stabilizing devices. For example, the leather or semi-rigid belt structure has a serious shortcoming in that it often times permits slippage resulting in vertical and lateral movement of the brace. The orthopaedic body jackets provide better support for the patient but are also subject to both slippage and improper positioning of the brace. These disadvantages deleteriously affect the proper functioning of the brace. Additionally, discomfort and pain have also been associated with the belts caused by pinching or excessive pressure on the skin or over bony protuberances causing skin breakdown.

Thus, there is a great need for improvements in hip abduction systems.

SUMMARY OF THE INVENTION

Accordingly, the present invention provides a hip abduction system for supporting a patient's hip joint comprising a substantially rigid pelvic girdle means positioned about a patient, a hip abduction means adjustably mounted to the pelvic girdle means for supporting a hip joint of a patient and a thigh engaging means connected to the hip abduction means for engaging a patient's thigh. The pelvic girdle means of the present invention comprises a first hip engaging means for engaging a first hip on one side of a patient's body and a second hip engaging means for engaging a second hip on the opposite side of the patient's body. The first and second hip engaging means have upper and lower flanges which are substantially contoured to the shape of a patient's body. The pelvic girdle also comprises front and back adjustment means which provide for precise positioning of the abduction system about a patient and over any bony protuberances. This feature will also prevent pain and skin breakdown. The pelvic girdle means also comprises a sliding guide means which provides vertical stability and integrity to the pelvic girdle means. This and other features substantially reduce both vertical and horizontal movement of the system about the patient which permits greater comfort and proper functioning.

According to another aspect of the present invention, the upper and lower flanges on the hip engaging means opposite the hip abduction means are longer than the other flanges, gaining purchase across the rib cage and the superior lateral edge and the thigh on the inferior lateral edge. This feature substantially eliminates migration of the abduction system about the patient and prevents the loss of abduction caused by the support displacing the soft tissue of the abdominal region. This feature also permits the overall size of the hip abduction system to be reduced.

The hip abduction system according to the present invention is constructed to prevent both lateral and vertical movement of the brace on the patient and which optimally supports the hip joint of a patient. Also, the brace is light weight and can be worn comfortably by the user both under normal conditions and while exercising or engaging in physical therapy, while still providing optimum support to the hip joint area.

DETAILED DESCRIPTION OF THE PREFERRED EMBODIMENT

Figure 1:
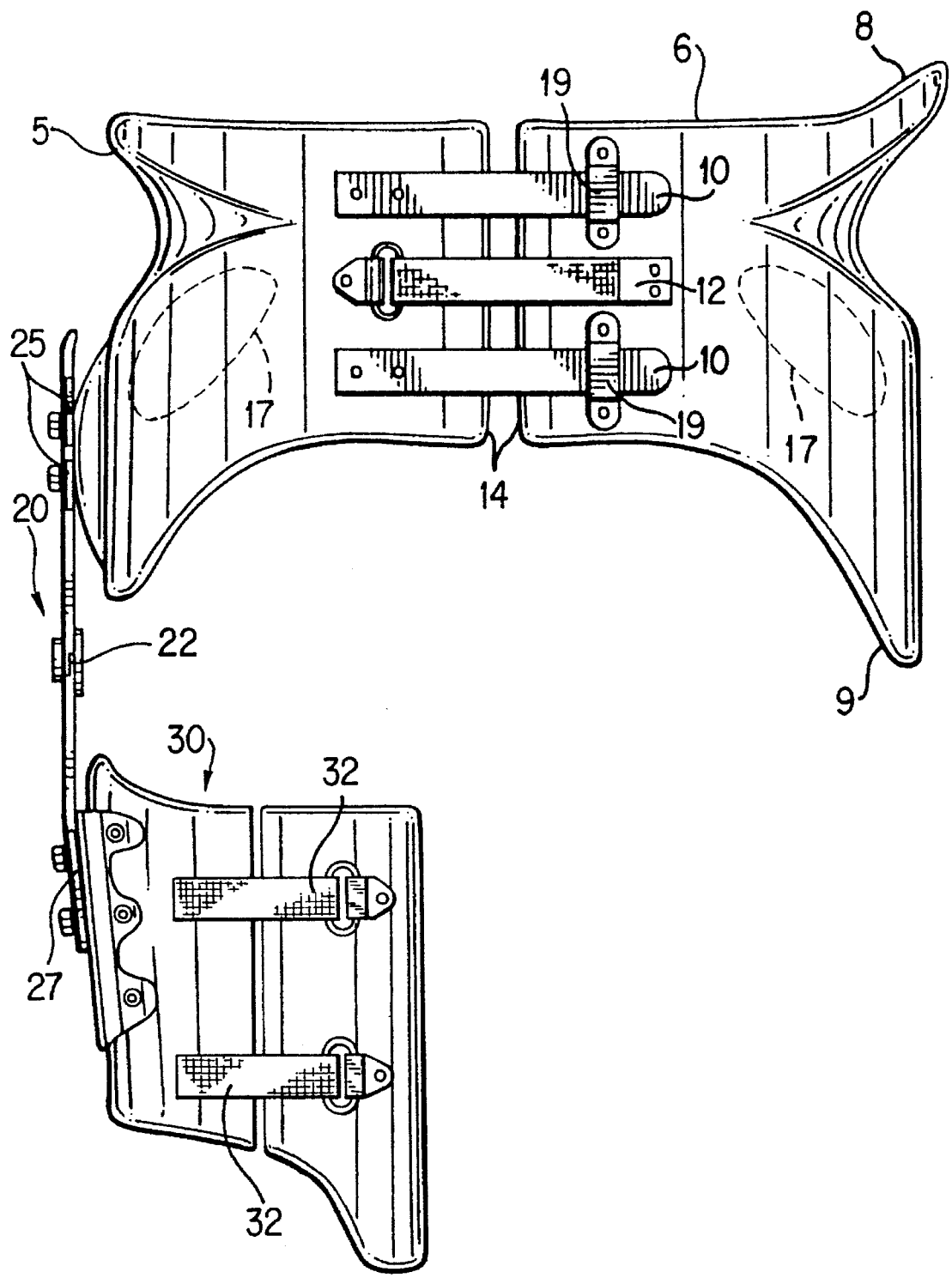
FIG. 1 is a front view illustrating the hip abduction system according to the present invention.

A hip abduction system, in accordance with one embodiment of the invention, for supporting the hip joint of a human patient will be discussed in detail with reference to FIG. 1 which shows a substantially rigid pelvic girdle means 1 for adjustably supporting the hip region of the patient. Pelvic girdle means 1 comprises a first hip engaging means 5 for engaging a first hip on one side of a patient's body and a second hip engaging means 6 for engaging a second hip on an opposite of a patient's body. The first and second hip engaging means are adapted to fit about the patient's hip region. First and second hip engaging means are also each constructed to fit about the patient's hip region and are fastened together by fastening means 12 near the center region of a patient's body. See FIGS. 1 and 2. In a preferred embodiment, fastening means 12 is a hook and pile strap. FIG. 1 also illustrates that the first and second hip engaging means are substantially contoured to the shape of a patient's hip or waist region. Providing the contoured first and second hip engaging means enables precise positioning of the brace on the front bony protuberances of a patient's hips. These features substantially eliminate both vertical and horizontal slippage of the brace about the patient.

Figure 2:
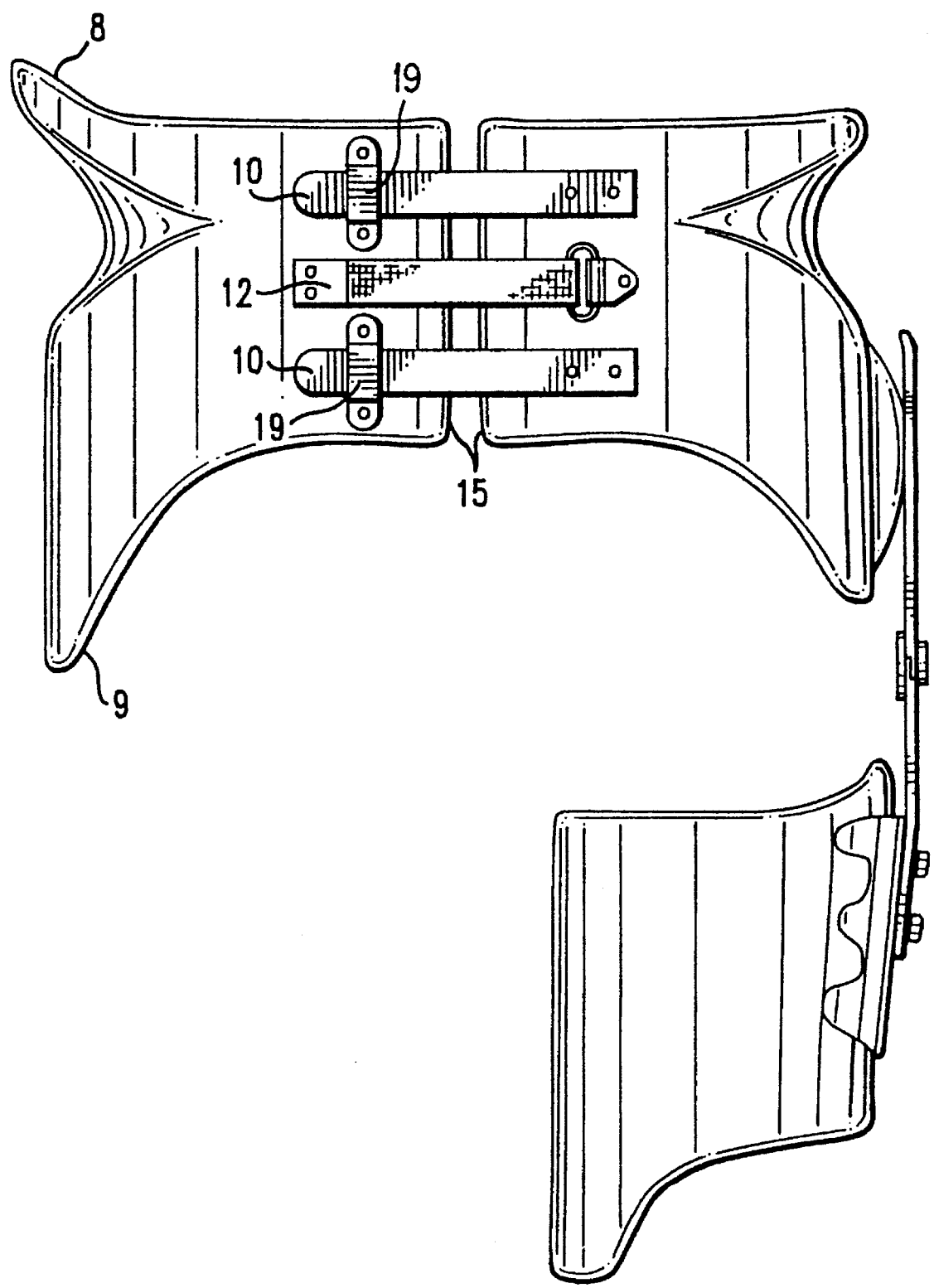
FIG. 2 is a rear view of the hip abduction system according to the present invention.

The pelvic girdle of the present invention is a "bi-valve" structure wherein the first hip engaging means 5 is a first valve of the bi-valve structure and the second hip engaging means 6 is a corresponding second valve of the bi-valve structure. As illustrated in FIGS. 1 and 2, the first and second valves extend about the opposite sides of the patient's body. Each valve has front end portion 14 and a back end portion 15 wherein the front end portion of the first valve is positioned adjacent the front end portion of the second valve at a front portion of a patient's body. The back end portion of the first valve is positioned adjacent the back end portion of the second valve near the back portion of the patient's body.

Pelvic girdle means 1 further comprises a slidable guide means 10 for facilitating the proper positioning of the hip engaging means 5 and 6 about a patient. In a preferred embodiment of the present invention, the slidable guide means is a substantially rigid sliding guide member which are slidable through channels 19, as shown in FIGS. 1 and 2. The substantially rigid slidable guide means 10 permits the hip support means to be precisely secured to the patient in any desired position. The slidable guide means 10 enables the pelvic girdle to be adjusted about the patient without vertical migration. This affords both vertical stability and integrity to the pelvic girdle means. This feature of the invention is particularly advantageous since patients often experience weight fluctuations while recovering from injuries which involve immobilization. The pelvic girdle can accommodate patients having Scoliosis by mounting the slidable guide means to accommodate a position over the anterior superior iliac spine (A.S.I.S.) or other bony protuberances to prevent pain and skin breakdown while insuring or maintaining the vertical stability and integrity of the pelvic girdle.

The slidable guide means 10 can be any suitable substantially rigid structure, such as a rigid plastic material or the like, which is slidable into and out of an open channel, such as channel 19.

In a preferred embodiment of the present invention, the pelvic girdle means comprises a slidable guide means on the rear portion thereof which secures the rear side of the first and second hip engaging means about the patient, as illustrated in FIG. 2. The slidable guide means illustrated in FIG. 2 can be the same slidable guide means described above in connection with FIG. 1. Providing front and rear slidable guide means enables a secure fit and substantially prevents any vertical movement of the pelvic girdle means on the patient. The slidable guide means on the posterior region of the pelvic girdle means enables the hip abduction system to be adjusted without vertical movement of the pelvic girdle on the patient.

The hip abduction system according to the present invention also comprises a waist support means positioned on the internal portion of the first and second hip engaging means 5 and 6. In a preferred embodiment, the waist support means comprises recesses 17, illustrated in fantom in FIG. 1, formed on an internal portion of the first and second hip engaging means for engaging the front bony protuberances of a patient's hips and facilitate proper positioning of the brace. In a most preferred embodiment, the internal ridge 17 is formed integrally with the first and second hip engaging means.

The pelvic girdle means 1 is constructed with any suitable substantially rigid material which will provide proper patient support but which will also allow flexation. In a preferred embodiment, the pelvic girdle means is constructed with a low density polyethylene material. To provide the desired support and comfort, the polyethylene material as used in a preferred embodiment is approximately 1/16" to 5/16" thick and, preferably, 3/16" thick. Also in a preferred embodiment, the pelvic girdle comprises an aliplast (foam liner) of approximately 1/16" to 1/4" and, preferably, approximately 1/8".

The hip abduction system of the present invention further comprises a hip abduction means 20 for supporting the hip joint of a patient, schematically illustrated in FIG. 1. The hip abduction means 20 comprises a metal caliper 22 which can be locked at a desired angle for a particular patient, and which supports the patient's weight when used and restricts the patient's range of motion. Hip abduction means 20 can be any suitable mechanism for supporting the patient's weight and locking the brace at a desired angle which are used in abduction systems of this type.

Metal caliper 22 is mounted at an upper region to either the first or second hip engaging means by any suitable means, such as appropriate screws. In a preferred embodiment, the upper portion of metal caliper 22 comprises channels 25 which enable the caliper to be adjustably mounted to the hip engaging means, as schematically illustrated in FIG. 1.

The hip abduction system according to the present invention further comprises a thigh engaging means 30 for engaging the patient's thigh and enabling proper support of the hip joint. Thigh engaging means 30 is contoured to the shape of a patient's thigh and is secured thereto by any suitable fastening means, such as by hook and pile straps 32 illustrated in FIG. 1. The thigh engaging means 30 is mounted to a lower end of metal caliper 22 by any suitable means, such as appropriate screws. In a preferred embodiment, the lower portion of metal caliper 22 has channels 27 which enable the caliper to be adjustably mounted to the thigh engaging means, as schematically illustrated in FIG. 1.

In accordance with a preferred embodiment of the present invention, the pelvic girdle comprises upper and lower flanges which substantially contour the shape of the patient's body. In a most preferred embodiment, the flanges on the hip engaging means opposite the abduction means, illustrated at 8 and 9 in FIG. 1, are longer than the other flanges of the other hip engaging means. Providing longer flanges on the hip engaging means opposite the abduction means substantially eliminates brace migration into the soft tissue of the abdominal region which enables the abduction system to function more properly by controlling the long level arm of the leg through the purchase of the rib cage and thigh instead of the soft tissue of the abdominal region. It also permits the system to be worn more comfortably by the patient.

In another preferred embodiment of the present invention, the flanges on both sides of the hip engaging means are initially of equal length and the flanges on the side opposite the abduction means, which ever side is selected, are then shortened, as illustrated by the hip abduction system of FIG.

1. This construction permits uniform construction of the pelvic girdle which can be adapted to support either hip joint of a patient.

The hip abduction system according to the present invention substantially supports the patient's weight thereby stabilizing and eliminating pressure from the patient's hip joint. The pelvic girdle of the present invention provides a bi-valve structure with front and rear slidable guide means which substantially eliminates vertical movement of the brace on the patient. Additionally, the longer upper and lower flanges on the hip engaging means opposite the abduction means substantially prevents the brace from migrating over the patient's body. By eliminating unwanted brace movement, the abduction system according to the present invention provides better support for a patient's hip joint and can be worn easily and comfortably.

Although the invention has been described in connection with certain embodiments, it is not limited to them. Modifications within the scope of the following claims will be apparent to those skilled in the art without derogating the scope of the applicants' novel contribution to the art.

What is claimed is:

1. A hip abduction system for stabilizing the hip joint of a patient, comprising:

a) a substantially rigid two-piece pelvic girdle comprising a first hip-engaging member dimensioned to fit a first hip on one side of the patient's body and connected by a fastening device to a second hip-engaging member dimensioned to fit a second hip on another side of the patient's body;

b) a slidable guide system mounted on said pelvic girdle and comprising a substantially rigid guide member disposed on one of said hip-engaging portions and engaging a channel disposed on another of said hip-engaging portions, whereby relative vertical movement between the hip-engaging portions is reduced;

c) a substantially rigid caliper device with an upper end and a lower end, said upper end adjustably mounted to one of said hip-engaging portions; and d) a substantially rigid thigh-engaging member, dimensioned to encircle the patient's thigh and adjustably mounted to said lower end of said caliper device, whereby a distance between the thigh-engaging member and the pelvic girdle can be adjusted by adjusting the relative positions of the thigh-engaging member and the pelvic girdle on said caliper device;

wherein said first and second hip-engaging members each comprise upper and said lower flanges, the upper end of said caliper device is mounted to said first hip-engaging member, and the upper and lower flanges of said second hip-engaging member are longer than the respective upper and lower flanges of said first hip-engaging member.

2. The hip abduction system according to claim 1, wherein said pelvic girdle comprises a slidable guide system mounted on each of a front and rear portion of said pelvic girdle.

3. The hip abduction system according to claim 1, wherein said first and second hip-engaging members each are contoured so as to conform to the shape of the patient's body.

4. The hip abduction system according to claim 3, wherein said caliper device comprises a channel member mounted to said first hip-engaging member.

5. The hip abduction system according to claim 4, wherein said caliper device further comprises a channel member mounted to said thigh-engaging member.

* * * * *